US012640267B2

(12) United States Patent
Khan et al.

(10) Patent No.: US 12,640,267 B2
(45) Date of Patent: May 26, 2026

(54) MEDICAL TREATMENT PLANNING SYSTEM AND METHOD WITH MACHINE LEARNING

(71) Applicants: Zaw Ali Khan, Uttar Pradesh (IN);
Mohsin Ali Khan, Uttar Pradesh (IN)

(72) Inventors: Zaw Ali Khan, Uttar Pradesh (IN);
Mohsin Ali Khan, Uttar Pradesh (IN)

( * ) Notice: Subject to any disclaimer, the term of this patent is extended or adjusted under 35 U.S.C. 154(b) by 96 days.

(21) Appl. No.: 17/777,984

(22) PCT Filed: Dec. 6, 2019

(86) PCT No.: PCT/IB2019/001286
§ 371 (c)(1),
(2) Date: May 18, 2022

(87) PCT Pub. No.: WO2021/111162
PCT Pub. Date: Jun. 10, 2021

(65) Prior Publication Data
US 2022/0351858 A1      Nov. 3, 2022

(51) Int. Cl.
*G16H 50/20*          (2018.01)
*G16H 10/60*          (2018.01)
(Continued)

(52) U.S. Cl.
CPC ............. *G16H 50/20* (2018.01); *G16H 10/60* (2018.01); *G16H 20/10* (2018.01); *G16H 20/60* (2018.01); *G16H 50/30* (2018.01); *G16H 70/40* (2018.01)

(58) Field of Classification Search
USPC .......................................................... 705/2
See application file for complete search history.

(56) References Cited

U.S. PATENT DOCUMENTS

2014/0278492 A1*  9/2014  Silver ................... G16H 50/20
                                                    705/2
2019/0251230 A1*  8/2019  Fernandez ........... C12Q 1/6886
2022/0383998 A1* 12/2022  Cossler ................ G16H 50/50

OTHER PUBLICATIONS

Zarepisheh et al ("Automated intensity modulated treatment planning: The expedited constrained hierarchical optimization (ECHO) system," Medical Physics, vol. 46, Issue 7, Jul. 2019, pp. 2944-2954) (Year: 2019).*

(Continued)

*Primary Examiner* — Christopher B Tokarczyk
(74) *Attorney, Agent, or Firm* — Offit Kurman; Tod A. Kupstas

(57) ABSTRACT

A decision support system that aids healthcare practitioners in making more informed clinical decisions and avoiding errors related to diagnosis and treatment of diseases. The system utilizes several data points from the patient history and clinical findings input by the patient and the doctor, to help the doctor make a more accurate diagnosis and develop a more informed treatment plan that incorporates not just drugs and procedures, but also dietary and lifestyle interventions. A system of the present disclosure comprises dosage calculator, symptom checker, differential diagnosis, drug interaction checker, side effect checker, nutritional analyzer and drug-food interaction checker input pathways and corresponding database compartments. Output data is generated in correspondence with patient input data and stored on a database server, where it is correlated with patient outcomes over time and improved through machine learning.

19 Claims, 3 Drawing Sheets

(51) Int. Cl.
  *G16H 20/10* (2018.01)
  *G16H 20/60* (2018.01)
  *G16H 50/30* (2018.01)
  *G16H 70/40* (2018.01)

(56) References Cited

OTHER PUBLICATIONS

Authorized Officer: Lee Young, International Search Report and the Written Opinion, International Patent Application No. PCT/IB2019/001286, Report Completion Date May 12, 2020, 8 pp.
Authorized Officer Cecile Chatel, International Preliminary Report on Patentability, International Patent Application No. PCT/IB2019/001286, Mail Date Jun. 16, 2022, 7 pp.

* cited by examiner

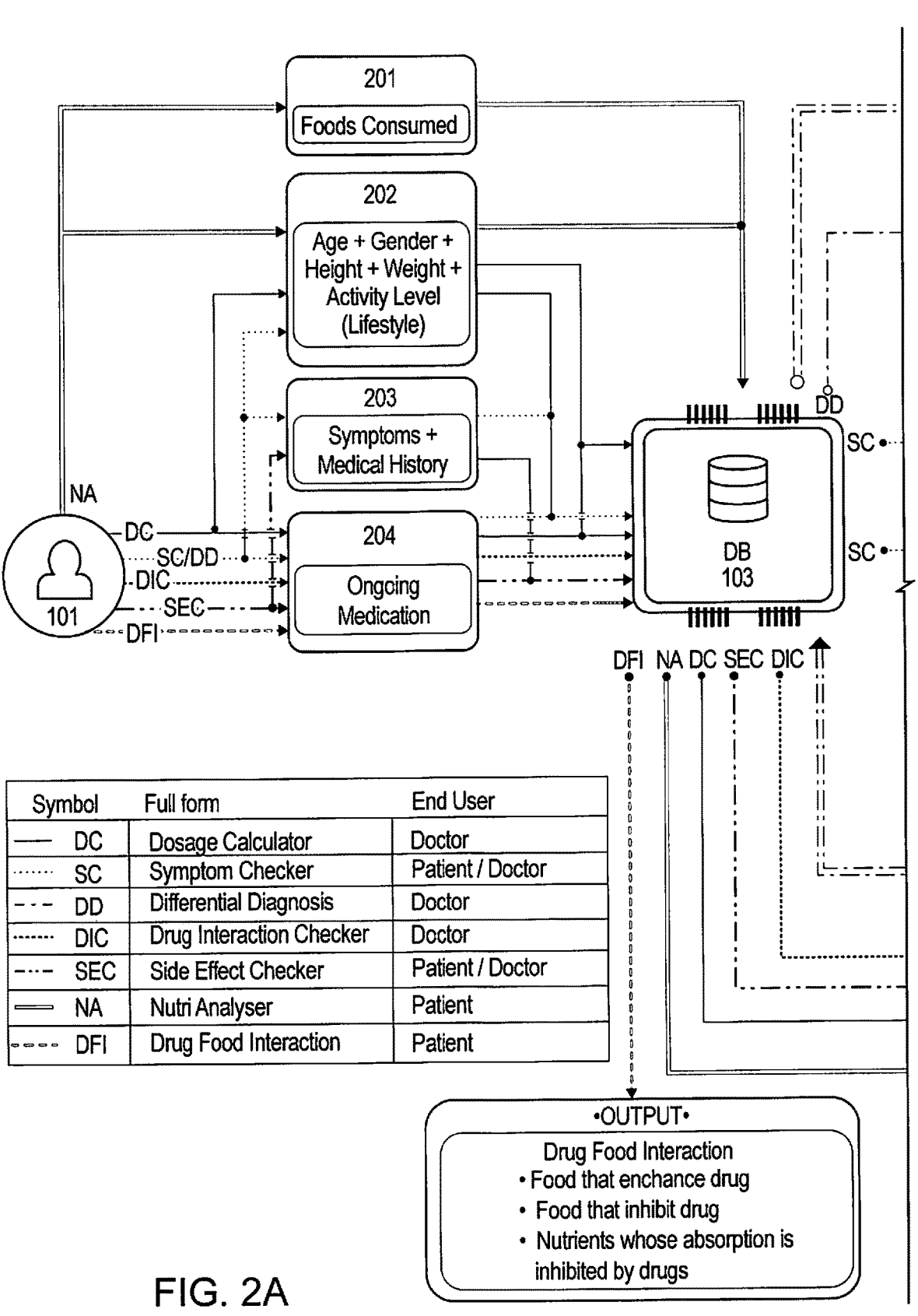

| Symbol | | Full form | End User |
|---|---|---|---|
| — | DC | Dosage Calculator | Doctor |
| ⋯⋯ | SC | Symptom Checker | Patient / Doctor |
| - - - | DD | Differential Diagnosis | Doctor |
| ·-·-·- | DIC | Drug Interaction Checker | Doctor |
| -·-·- | SEC | Side Effect Checker | Patient / Doctor |
| ═══ | NA | Nutri Analyser | Patient |
| - - - - | DFI | Drug Food Interaction | Patient |

·OUTPUT·

Drug Food Interaction
• Food that enchance drug
• Food that inhibit drug
• Nutrients whose absorption is inhibited by drugs

FIG. 2A

MEDICAL TREATMENT PLANNING SYSTEM AND METHOD WITH MACHINE LEARNING

STATEMENT REGARDING FEDERALLY SPONSORED RESEARCH

The invention of the present disclosure was developed without federal funding.

BACKGROUND OF THE INVENTION

Medication prescription errors, which are all too common, are a major contributor to avoidable morbidity and mortality. The World Health Organization (WHO) has published several key factors thought to influence the frequency of medication errors. Errors originating from healthcare professionals arise from lack of training, lack of knowledge and experience, inaccurate perception of risk, fatigue, health issues affecting judgment and poor communication skills in the context of patient interactions. Patient factors such as poor literacy or language barriers can contribute to misunderstandings in the clinic that lead to medication errors. Other factors such as like-sounding or -appearing drug names and unintuitive selection systems also contribute to error rates.

Medication errors can lead to nonspecific treatment regimens which may result in prescription of drugs that cause undesirable side effects with minimal efficacy with respect to the underlying medical condition or result in adverse drug events. It is estimated that about half of adverse drug events result from preventable medication errors. Adverse drug events account for nearly 700,000 emergency room visits per year and 100,000 hospitalizations. Thus, there is a need in the art for systems and methods useful in reducing the frequency of medication errors and in turn adverse drug events.

While medical library information that could be used to reduce medication errors and tailor treatments better to underlying conditions is difficult to access in its current state, and medical science is continuously evolving, giving rise to the need for real time access to information useful in medical treatment planning. It is an object of the invention of the present disclosure to leverage information from products like encyclopedias of medical science in order to compile every known medical phenomenon into a single and user-friendly platform that can be accessed by doctors, nurses, patients, medical students, researchers or public in general. The invention of the present disclosure provides a system and methods that supplement the doctors' knowledge by providing real-time alerts and suggestions based on real-time inputs and the vast medical science databank of medicines, diseases and food products.

SUMMARY OF THE INVENTION

The invention of the present disclosure provides a one of a kind decision support system that aids healthcare practitioners and patients alike in making more informed clinical decisions and avoiding errors related to diagnosis, treatment of diseases and planning and monitoring of rehabilitation. The system utilizes several data points from the patient history and clinical findings input by the patient and the doctor to help the doctor make a more accurate diagnosis and develop a more informed treatment plan that incorporates not just drugs and procedures, but also dietary and lifestyle interventions.

In one embodiment, the invention is that of a system comprising of a user interface where a user may input data related to a patient's diet, age, gender, height, weight, medical history, lifestyle, pregnancy status (for females of fertile age), current symptoms and ongoing medications. The user interface may be in communication with a module tangibly stored on a non-transitory computer readable medium comprising instructions which when executed cause a processor to generate a number of outputs useful in treatment planning.

Outputs of the system useful in treatment planning may include recommendations for laboratory tests or other investigative measures for diagnosis and possible disease conditions of a patient ranked according to probability. The system is useful in developing artificial intelligence useful for improved disease diagnosis by compiling input data from multiple patients over time as well as diagnostic accuracy data associated with the patients that is input into the system after diagnosis and treatment. An artificial intelligence output of a system of the present disclosure is an optimized list of possible disease states of a patient ranked based on probability that factors in diagnostic accuracy and treatment success rates of input patient data over time.

Another system output of an embodiment of the present disclosure is a list of proposed treatment options including recommended procedures, recommended lifestyle adjustments or changes, dietary recommendations and information on drugs useful in treating an identified disease state. The results of diagnostic laboratory investigations are input into a database in communication with a module of the present invention so that the efficacy of the system may be continuously improved over time.

Another system output of an embodiment of the present disclosure comprises key information on any recommended therapeutic measures including information on drugs useful in treating an identified disease state. Drug information may include safety warnings such as known dosage limits, drug-drug interactions, drug-food interactions and side effects and a list of alternative therapies to those drugs for which safety concerns are raised for individual patients and recommended dosages of recommended drugs. A further system output of the present disclosure is a nutritional intake reporting feature that results from analysis of dietary input data and associates various nutrient intakes with positive and negative patient outcomes to improve holistic patient diagnoses. Moreover, based on the prescription of a patient, the system informs about the possible interactions of the prescribed drugs with any food substances. Such drug-food interactions can be of three types: (1) Decreased absorption of certain drugs due to intake of certain foods; (2) Increased absorption of drugs due to intake of certain foods; (3) Decreased absorption of certain nutrients due to the intake of certain drugs.

These and other aspects of the invention will be appreciated by one of ordinary skill in the art. Embodiments of the system and methods of the present invention are described in further detail in the drawings and detailed description that follows.

BRIEF DESCRIPTION OF DRAWINGS

FIGS. 2A-2B are a detailed flow diagram of a method and system components of the present disclosure.

DETAILED DESCRIPTION OF THE INVENTION

Figure 1:
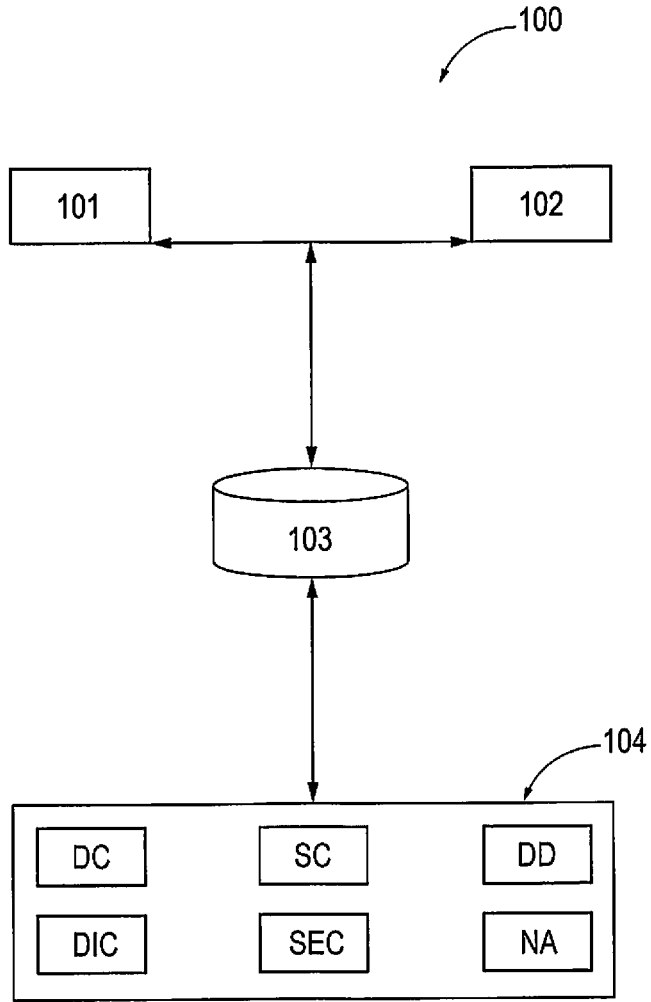
FIG. 1 is a schematic of a system according to the present disclosure.

An embodiment of the invention is best illustrated with reference to the accompanying drawings. FIG. 1 is a schematic representation of a three-tier (3T) system architecture according to the present disclosure 100, with user interface (UI) 101 for the input of data into the system, the UI 101 being in communication with a database server 103 having a database comprising compartments for containing data entered by a user or pulled from reference sources, such as medication dosages, patient symptoms, diagnoses, known drug interactions, known side effects and nutritional information. A software application comprises tangibly stored instructions on a non-transitory computer readable medium such as an application server 104, which when carried out by a processor convert the various inputs into treatment planning outputs that may be accessed by a medical professional on a UI 101. The software application includes the following modules: dosage calculator (DC), symptom checker (SC), differential diagnosis tool (DD), drug interaction checker (DIC), side effect checker (SEC), nutritional analyzer (NA) and drug food interaction checker (DFI). Controllers 102 control requests and responses from the UI 101 after communication with the database server 103. All servers and controllers may reside at the same or different locations.

Referring still to FIG. 1, a UI 101 is provided for the input of data into a system as described herein for the purpose of executing the companion methods. The UI 101 may be accessed via a computing means with display and data entry functions such as a computer, tablet or smartphone. In one embodiment, the UI 101 may be included in a portable kiosk, such as might be suitable for installation at health clinics, doctor's offices and the like. The UI 101 is in communication with at least one server or equivalent computer readable medium for non-transitory data storage such as a database server 103 comprising a database segmented into several compartments based on the type of data entered.

Data is routed in a compartment-specific manner to be processed by a processor as instructed by a software modules residing on application server 104 that causes the processor to compile data inputs from multiple patients and correlate them with data compiled from medical library resources such as medical encyclopedias in order to produce various tools accessible to the medical practitioners seeking to develop treatment plans based on the information presented by their patients in view of the data compiled within the database from a broad swath of patients sharing symptoms or other attributes in common with the patient to be treated.

Figure 2B:
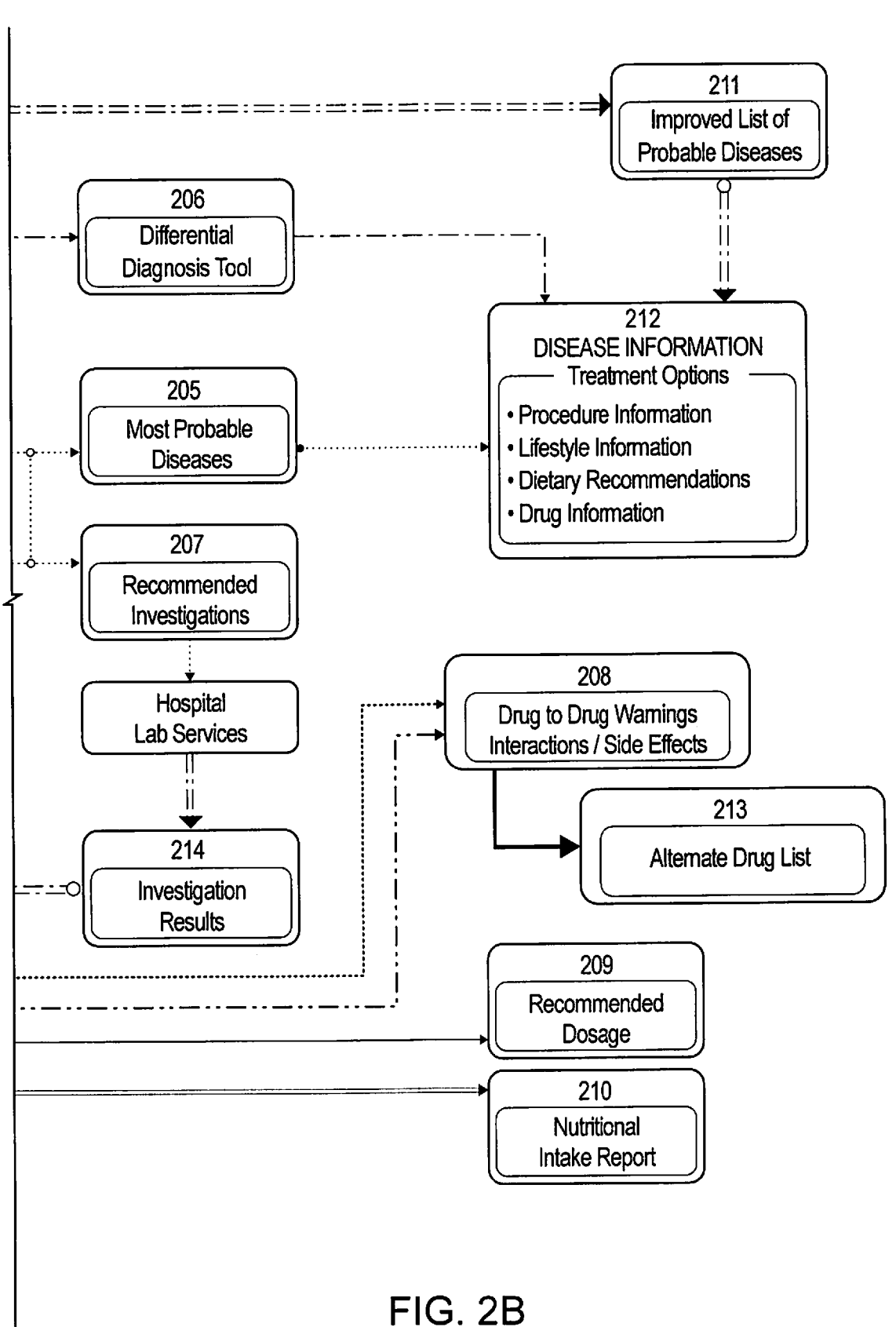

FIGS. 2A and 2B together consist of a detailed flow diagram of a method of interaction between the various software modules and the database and system components of the present disclosure, showing the flow of data from the UI 101 in communication with a database (DB) residing on a database server 103 in communication with an application server comprising each software module of the present invention that in turn causes a processor to generate outputs visible at the UI 101, which may comprise multiple UIs, such as a UI of a registration kiosk at a doctor's office, or a UI available on a computer or handheld device issued to a doctor or allied health practitioner. The various inputs shown in FIG. 2A via the output pathways shown in FIG. 2B provide a high-level overview of the categories of data that may be input through the various data entry and compilation pathways of the system.

Data input into the UI 101 comprises patient data, such as but not by way of limitation dietary information such as nutrient intake or foods consumed; demographic data such as age and gender; physical data such as height and weight; medical information specific to the patient such as personal and family medical history, current symptoms and any ongoing medications being taken; and following any investigations conducted in connection with disease diagnosis, information on the results of such investigations.

In an embodiment of the present disclosure, a dedicated kiosk comprises a UI 101 where a patient can enter all inputs at the time of registration. If the patient is unable to enter any details at that time, vitals such as height, weight, pulse rate and blood pressure can be automatically measured at the kiosk through integrated hardware and input into the system. Alternatively, a medical technician at the office where the kiosk is located may input the data after measurement. Either the patient or the doctor or staff can enter symptom information at any time during an office visit. Preferably the patient enters data at the time of registration, but the system and methods described herein allow for alternative methods of data entry.

Turning now to FIG. 2A, a visual data flow diagram of a system of the present disclosure comprising a UI 101 for entry of multiple inputs 201-204, at least one database server 103, at least one DB residing on the at least one database server 103 or equivalent, and at least one software module DC, SC, DD, DIC, SEC, DFI and NA comprising instructions for generating various outputs 205-212. One of ordinary skill in the art will appreciate that at least one database and the software modules may reside on the same or different servers or equivalent so long as they are configured for communication between them.

Inputs include patient diet information 201, patient vitals 202, symptoms and medical history 203 and patient medications 204. Input pathways comprise DC, SC, DD, DIC, SEC and NA. DC compartmentalizes the demographic and physical input data from a user (i.e., doctor) within the database DB, where it may be processed to generate an output related to recommended dosage of one or more recommended drugs. SC compartmentalizes the same data within the DB in addition to input information related to symptoms, medical history and ongoing medications of a patient. In one embodiment, data may be entered into the SC by a patient or doctor. A DD of the present invention compartmentalizes the same data as SC and is accessed to be correlated with disease conditions associated with the symptoms identified and input by a doctor, along with medical history input by the same.

A DIC of the present invention provides a data entry point for a doctor or health practitioner to enter specific patient medication information and check for drug-drug interactions with any recommended therapeutics. The same information along with symptoms may be entered by a doctor or patient into an SEC for compartmentalization and access in order to identify known side effects associated with any recommended medications. NA is provided to allow a patient to enter information related to the patient's diet (i.e. names and quantities of consumed food items), along with patient's age, gender, height, weight and physical activity level so that the data may be accessed and correlations with patient outcomes may be monitored for the purpose of determining whether any dietary changes might improve patient outcomes. It determines the nutritional achievement of the patient for the input meal or set of meals, along with pointing out the nutrients and active constituents that are in the foods consumed.

Outputs of the system useful in treatment planning may include recommended investigations 207 such as laboratory tests or other investigative measures for diagnosis and possible disease conditions of a patient ranked according to probability. Investigation results 214 are retained and input back into the DB for improved future recommendations correlating with patient success. The system is useful in developing artificial intelligence useful in improved disease diagnosis by compiling input data from multiple data over time as well as diagnostic accuracy data associated with the patients that is input into the system after diagnosis and treatment. An artificial intelligence output of a system of the present disclosure is an improved list of possible disease states, including most probable diseases 205 and an improved disease list 211 generated by application of DD to most probable diseases 205 information, ranked based on probability that factors in diagnostic accuracy and treatment success rates of input patient data over time.

Another system output of an embodiment of the present disclosure is a list of proposed treatment options 212 including recommended procedures, recommended lifestyle adjustments or changes, dietary recommendations and information on drugs useful in treating an identified disease state. All the information provided also contains the details of the medical literature from which the information has been sourced. URL links are also provided, if available.

The dietary recommendations are based on the symptoms, diagnosis prescriptions and allergies. These recommendations are of two types: (1) recommended foods and (2) foods that are to be avoided. The recommended foods are those that have been established as beneficial (for the input condition) in medical and nutritional literature. Similarly, the foods to be avoided are those that have been established to be detrimental (for the input condition). The relevant nutrient or active constituent is specified for every dietary recommendation. For each of the nutrient and active constituent, the system provides comprehensive information such as:

(a) its biochemical mechanism that is relevant to the condition (b) its recommended dietary allowance (RDA)

(c) its concentration in the various foods (d) the effect of its deficiency and its toxicity (e) its interactions, if any, with prescribed medicines (f) its interaction with any other active constituents or nutrients that may inhibit or enhance its absorption or action (g) its time of peak plasma concentration (i.e. $T_{max}$)

(h) its biological half-life (i.e. t½)

(i) the temperature limit in which it remains stable (j) the recommended preparation method based on the temperature limit.

The drug information output provides comprehensive information about each drug, viz.

(a) its generic name and active ingredient (b) drug category (c) brand names by which the drug is available (d) its indications or uses (e) route of administration (f) recommended dose (based on patient's details)

(g) its trough value (h) its mechanism of action (i) its route of excretion (j) its side effects (k) its contraindications and alternate drugs (l) list of drugs with which it interacts; mechanisms of the interactions;

(m) food substances that contain a nutrient or active constituent that may enhance the absorption or action of the drug (n) food substances that contain a nutrient or active constituent that may inhibit the absorption or action of the drug (o) its time of peak plasma concentration (i.e. $T_{max}$)

(p) its biological half-life (i.e. t½)

The results of diagnostic laboratory investigations are input into a DB in communication with a software module of the present invention so that the efficacy of the system may be improved over time.

Another system output of an embodiment of the present disclosure comprises drug warnings 208 as well as recommended dosage 209 for any recommended therapeutic measures. Drug warnings 208 may include safety warnings such as known drug-drug interactions, contraindications and side effects and an alternative drug list 213 to those raising safety concerns for individual patients and recommended dosages of recommended drugs. A further system output of the present disclosure is a nutritional intake report 210 feature that results from analysis of dietary input data and associates various nutrient intakes with positive and negative patient outcomes to improve holistic patient diagnosis and treatment plans.

Machine learning is employed in a few key areas by a system of the present disclosure. Improved prescription suggestions can be obtained based on the details of patients' vitals entered into the UI, signs and symptoms retrieved from both registration and doctor's input data, the diagnosis (entered by the doctors) and the investigation results. The system refines its output with each occurrence and learns to give better and more precise overall treatment recommendation. It can also develop an antibiogram to give better antibiotic suggestions as it learns from details such as geographic location of the patient and bacterial strain and antibiotic sensitivity data (i.e., microbiology test results input into the DB following investigation). Improved diagnosis suggestions are made possible based on the same inputs.

A system of the present invention can also improve on suggesting possible communicable diseases based on information such as address of the patient, travel history of the patient (if the patient has recently travelled), incubation periods of communicable diseases (taken from a database of communicable diseases), weather pattern (automatically queried from the Internet based on the travel location and time period of travel; this information is useful for ruling out or suggesting bacteria based on the temperature ranges that they thrive in).

Improved investigation suggestions are also made possible with the help of machine learning based on the patients' vitals, signs and symptoms and diagnostic inputs.

These and other aspects of the invention will be appreciated by one of ordinary skill in the art. Embodiments of the system and methods of the present invention are described in further detail in the drawings and detailed description that follows.

What is claimed is:

1. A medical treatment optimization system comprising:
at least one user interface for entering patient input data;
at least one database, the at least one database being tangibly stored on a non-transitory computer readable medium and in communication with the at least one user interface,
wherein the at least one database comprises a plurality of compartments corresponding to types of data, wherein patient input data is routed in a compartment-specific manner to the plurality of compartments corresponding to types of data;
a plurality of software modules tangibly stored on a separate application server, each of the plurality of software module comprising instructions which when executed cause a processor to:

compile patient input data from multiple patients, the patient input data from multiple patients taken from at least one of the plurality of compartments corresponding to types of data;

correlate compiled patient input data from multiple patients taken from at least one of the plurality of compartments corresponding to types of data with medical resources; and generate a first treatment plan for a patient based on correlated compiled patient input data from multiple patients taken from at least one of the plurality of compartments corresponding to types of data with medical resources.

2. The medical treatment optimization system of claim 1, wherein the patient input data comprises nutritional data, demographic data, physical data, medical history data and drug intake data.

3. The medical treatment optimization system of claim 1, wherein at least one of the software modules is adapted to develop a second treatment plan comprising an antibiogram developed from the first treatment plan.

4. The medical treatment optimization system of claim 1, wherein the at least one software module is selected from the group consisting of a dosage calculator, symptom checker, differential diagnosis tool, drug interaction checker, side effect checker, nutritional analyzer and drug food interaction checker.

5. The medical treatment optimization system of claim 1, wherein a second treatment plan different from the first treatment plan is generated by further compiling of patient input data from multiple patients.

6. The medical treatment optimization system of claim 5, wherein at least one of the plurality of compartments can be accessed by more than one software module.

7. The medical treatment optimization system of claim 6, wherein the types of data comprises ongoing medications of the patient and at least one of the age, gender, height and weight of the patient and is compiled by a dosage calculator software module.

8. The medical treatment optimization system of claim 6, wherein the types of data comprises the age, gender, height, weight, symptoms, medical history and ongoing medications of the patient and is compiled by a symptom checker software module.

9. The medical treatment optimization system of claim 6, wherein the types of data comprises age, gender, height, weight, symptoms, medical history and ongoing medications of the patient and is compiled by a differential diagnosis tool software module.

10. The medical treatment optimization system of claim 6, wherein the types of data comprises ongoing medications of the patient and is compiled by a drug interaction checker software module.

11. The medical treatment optimization system of claim 6, wherein the types of data comprises ongoing medications, medical history and symptoms of the patient and is compiled by the side effect checker software module.

12. The medical treatment optimization system of claim 6, wherein the types of data comprises age, gender, height, weight, activity level, lifestyle and foods consumed by the patient and is compiled by the nutritional analyzer software module.

13. The medical treatment optimization system of claim 6, wherein the types of data comprises ongoing medications and is compiled by the drug food interaction software module.

14. The medical treatment optimization system of claim 1, wherein results of the first treatment plan are used to modify subsequent treatment plans.

15. A method of medical treatment optimization comprising:

accessing a system comprising;

a user interface for entering patient input data;

at least one database, the at least one database being tangibly stored on a non-transitory computer readable medium and in communication with the at least one user interface, a plurality of compartments corresponding to types of data;

a plurality of software modules tangibly stored on a separate application server;

routing patient input date in a compartment-specific manner to the plurality of compartments corresponding to types of data compiling patient input data from multiple patients taken from at least one of the plurality of compartments corresponding to types of data;

correlating compiled patient input data from multiple patients taken from at least one of the plurality of compartments corresponding to types of data with medical resources; and generating a first treatment plan for a patient based on correlated compiled patient input data from multiple patients taken from at least one of the plurality of compartments corresponding to types of data with medical resources.

16. The method of claim 15, providing a visual output, wherein the visual output comprises the first treatment plan and at least one URL related to the first treatment plan.

17. The method of claim 15, further comprising generating an antibiogram based on correlated complied patient input data from multiple patients.

18. The method of claim 15, further comprising generating an antibiogram based on correlated compiled patient input data from multiple patients.

19. The method of claim 15, further comprising generating information related to drug and food interaction based on correlated compiled patient input data from multiple patients.

\* \* \* \* \*